US00PP33593P2

(12) United States Plant Patent
Los et al.

(10) Patent No.: US PP33,593 P2
(45) Date of Patent: Nov. 2, 2021

(54) ***MANDEVILLA* PLANT NAMED 'PATMANROS2'**

(50) Latin Name: ***Mandevilla sanderi* (Hemsl.) Woodson**
Varietal Denomination: PATMANROS2

(71) Applicant: Patio Plants V.O.F., Klazienaveen (NL)

(72) Inventors: Martijn Los, Klazienaveen (NL); Maurits van den Arend, Klazienaveen (NL)

(73) Assignee: Patio Plants V.O.F., Klazienaveen (NL)

( * ) Notice: Subject to any disclaimer, the term of this patent is extended or adjusted under 35 U.S.C. 154(b) by 0 days.

(21) Appl. No.: 17/238,707

(22) Filed: Apr. 23, 2021

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./226, 232
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Mandevilla* plant named 'PATMANROS2' which is characterized by an upright and freely branching growth habit, an abundance of dark green foliage, light pink flowers with a dark pink floral tube, flowers with a large and symmetrical diameter, as well as the stability of these characteristics from generation to generation.

3 Drawing Sheets

Latin name of the genus and species: The Latin name of the genus and species of the novel variety disclosed herein is *Mandevilla sanderi* (Hemsl.) Woodson.

Variety denomination: The inventive variety of *Mandevilla* disclosed herein has been given the variety denomination 'PATMANROS2'.

CROSS REFERENCE TO RELATED APPLICATIONS

This application claims priority to the Community Plant Variety Rights application number 2020/1115, filed Apr. 23, 2020, which is herein incorporated by reference.

BACKGROUND OF THE INVENTION

Parentage: The new plant originated as a whole plant mutation which was discovered in March of 2017 growing amongst a plurality of cultivated unnamed *Mandevilla sanderi* plants. The discovery was made by the inventors at a greenhouse in Klazienaveen, The Netherlands. The true parentage of the claimed plant is not known. The mutation was observed to exhibit a unique flower relative to all other plants in the cultivated area and was isolated to confirm the stability and uniqueness of the characteristics first observed. In March of 2018, the claimed plant was selected for commercialization.

Asexual Reproduction: Asexual reproduction of the new cultivar 'PATMANROS2', by way of softwood stem cuttings, was first initiated in March of 2018 in Klazienaveen, The Netherlands. Through more than 6 subsequent generations, the unique features of this cultivar have proven to be stable and true to type.

SUMMARY OF THE INVENTION

The cultivar 'PATMANROS2' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PATMANROS2'. These characteristics in combination distinguish 'PATMANROS2' as a new and distinct *Mandevilla* cultivar:

1. *Mandevilla* 'PATMANROS2' exhibits an upright, freely branching growth habit; and
2. *Mandevilla* 'PATMANROS2' exhibits an abundance of dark green foliage; and
3. *Mandevilla* 'PATMANROS2' exhibits light pink flowers with a dark pink corolla tube.
4. *Mandevilla* 'PATMANROS2' exhibits a very open floral aspect which gives flowers a relatively large and symmetrical diameter.

BOTANICAL DESCRIPTION OF THE PLANT

Figure 1:
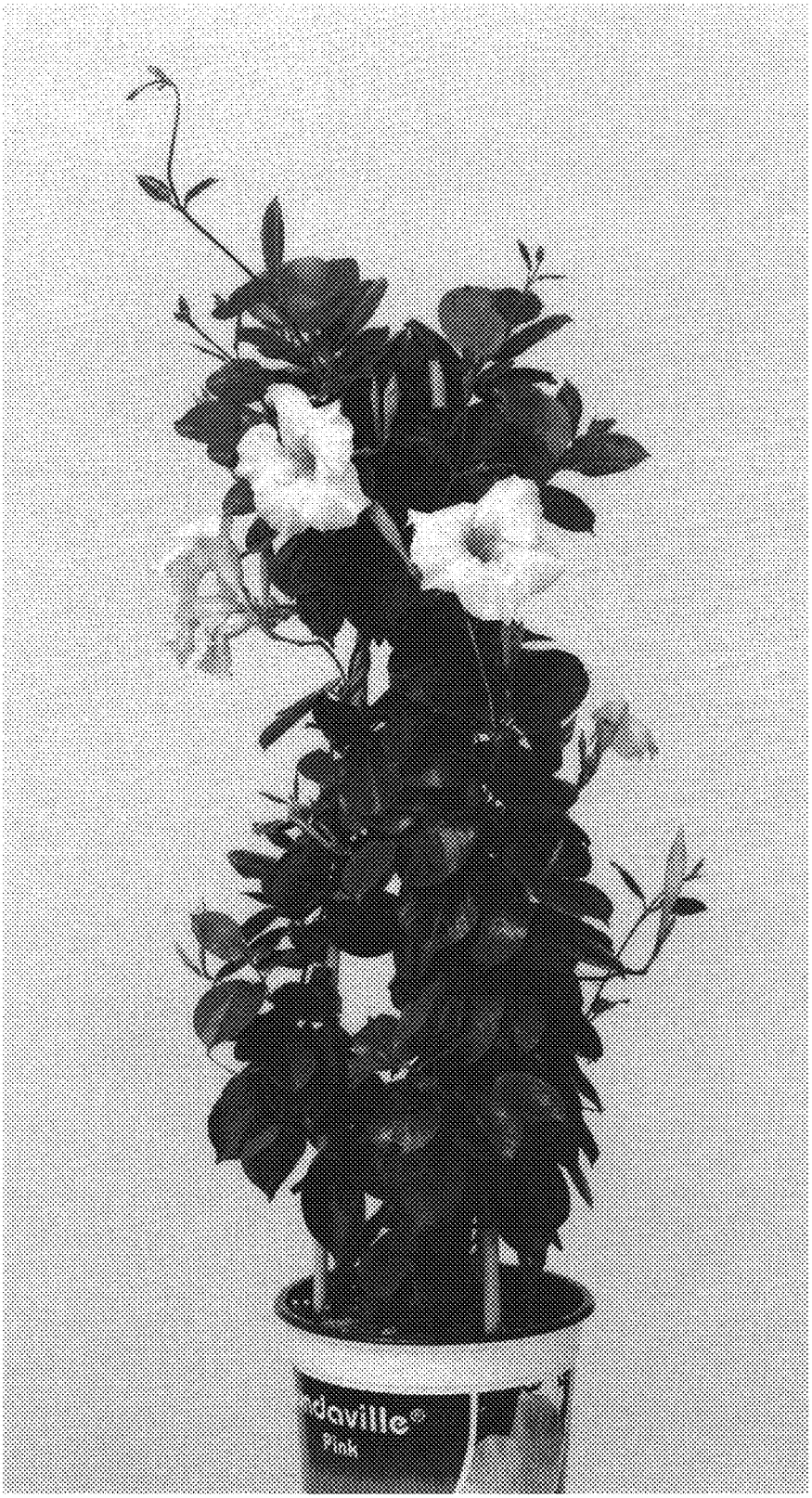
FIG. 1 illustrates, as nearly true as it is reasonably possible to make the same in color photographs of this type, an exemplary 12 month old 'PATMANROS2' plant in a 17 cm nursery pot, grown in a greenhouse in Klazienaveen, The Netherlands.
Figure 2:
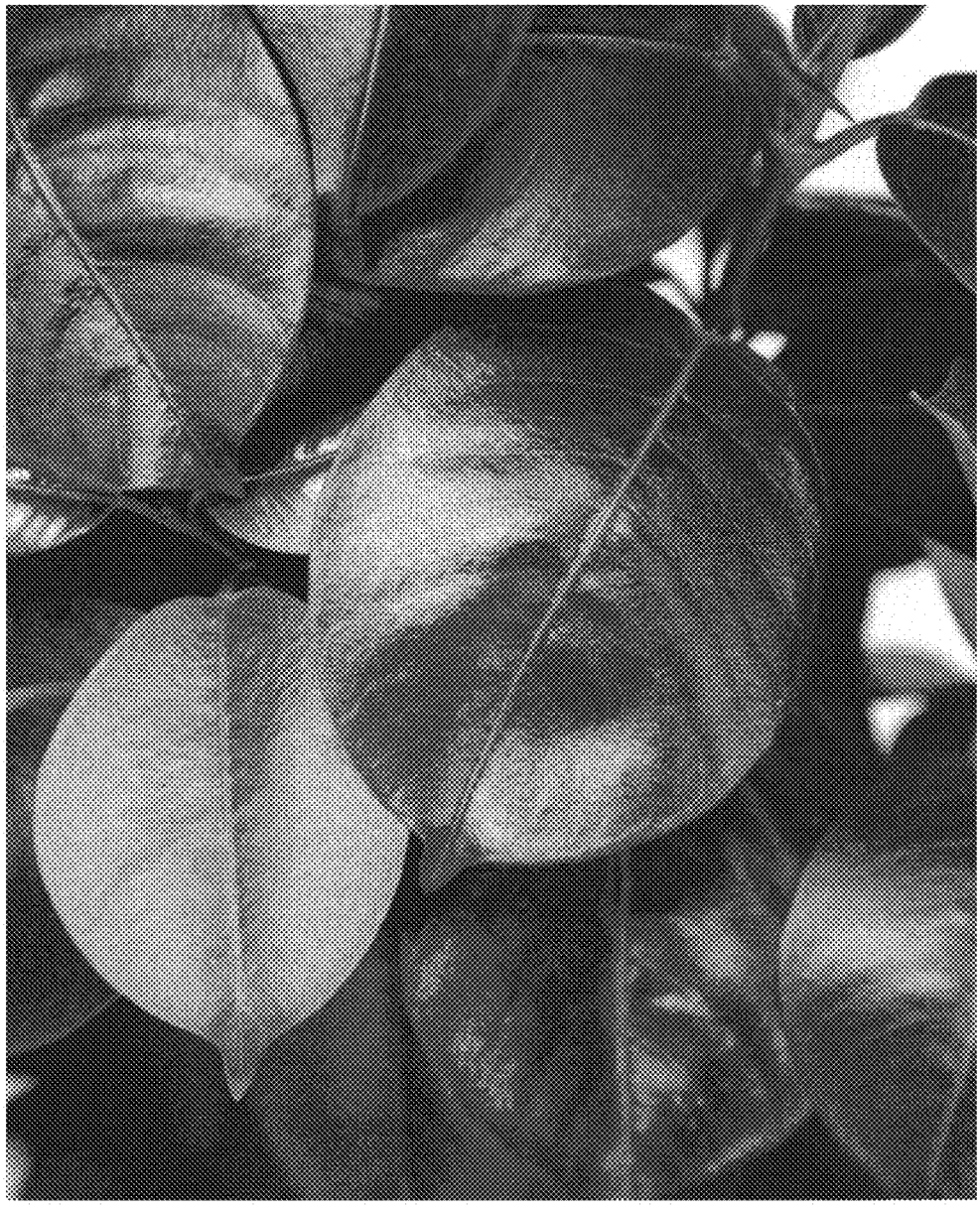
FIG. 2 illustrates, as nearly true as it is reasonably possible to make the same in color photographs of this type, the mature foliage of 'PATMANROS2'.
Figure 3:
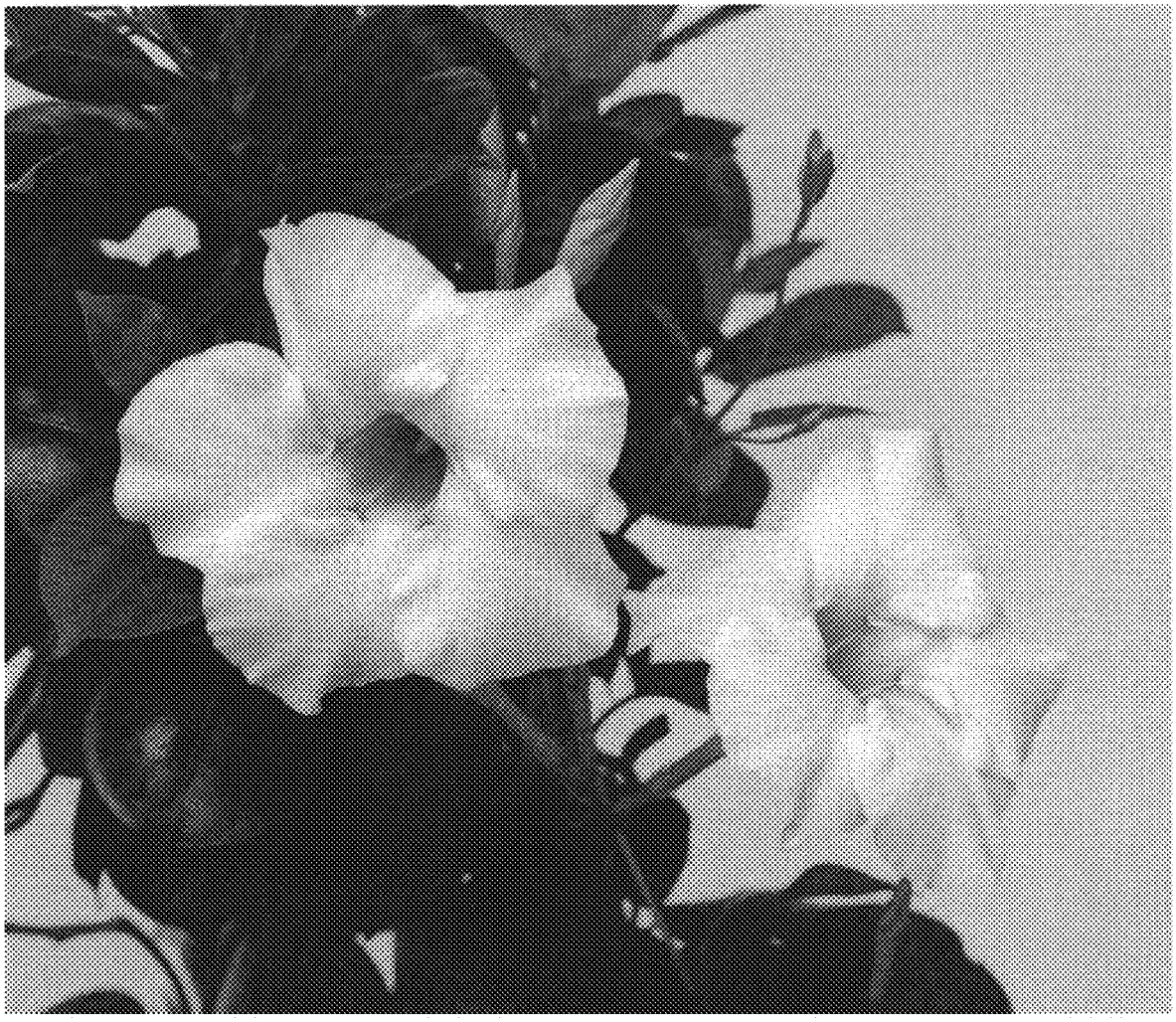
FIG. 3 illustrates, as nearly true as it is reasonably possible to make the same in color photographs of this type, an exemplary flower of 'PATMANROS2'.

The following observations and measurements were made in March of 2021 and describe averages from a sample set of six specimens of 12 month-old 'PATMANROS2' plants grown in 17 cm nursery pots grown in a greenhouse in Klazienaveen, The Netherlands. Plants were produced using conventional greenhouse production protocols for *Mandevilla* which consisted of regular overhead and ebb and flood irrigation and fertigation applications. Pest or disease control measures were utilized in production as required. Plants were produced with full sun exposure and no photoperiodic treatments or artificial light was given to the plants.

Those skilled in the art will appreciate that certain characteristics will vary with older or, conversely, with younger plants. 'PATMANROS2' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2015 (sixth edition).

A botanical description of 'PATMANROS2' and comparisons with the parent and most similar commercial variety of *Mandevilla* are provided below.

Plant description:

*Growth habit.*—Vining perennial; broad upright.

*Plant shape.*—Obovate to broad obovate.

*Average height from base to top of foliage.*—72.0 cm.

*Average height from base to top of the floral plane.*—64.0 cm.

*Average width.*—52.8 cm.

*Growth rate.*—Moderately fast growing.

*Plant vigor.*—Moderately vigorous.

*Propagation method.*—Softwood stem cuttings; rooting is in initiated in approximately 21 days, with a fully rooted cutting in approximately 6 weeks, when grown in a greenhouse with an ambient average temperature of 28 to 30 degrees Celsius.

*Time to produce a finished plant.*—Approximately 9 to 12 months is required to produce a fully rooted and marketable 19 cm plant when grown under greenhouse conditions.

*Disease and pest resistance or susceptibility.*—Plants have not been observed to be susceptible or resistant to pathogens and pests common to *Mandevilla sanderi*.

*Environmental tolerances.*—Adapt to at least USDA Zones 10 and 12, and temperatures ranging from at least 5 degrees to 40 degrees Celsius; moderate tolerance to rain; low to moderate tolerance to wind; low tolerance to drought.

Root system:

*General.*—Freely branching; moderately dense rooting.

*Texture.*—Fibrous.

*Color.*—Light brown.

Stem:

*Branching habit.*—Basally branching main stem; freely branching with lateral branches. Stems and branches exude a milky exudate when damaged.

*Number of main stems per plant.*—5.

*Number of lateral branches per plant.*—18.

*Aspect.*—Rounded.

*Length of lateral branches.*—32.9 cm.

*Diameter of lateral branches.*—0.35 cm at the widest point.

*Internode length on lateral branches.*—7.4 cm.

*Attitude.*—Upright; angle is approximately 30 degrees from vertical.

*Strength.*—Strong.

*Texture and luster.*—Glabrous and moderately glossy.

*Color, juvenile.*—Yellow-green, nearest to RHS 146C.

*Color, mature.*—Yellow-green, nearest to RHS 144A; surfaces exposed to sunlight are greyed-orange, nearest to in between 166A and 166B.

*Color at internodes.*—Yellow-green, nearest to RHS 144A; surfaces exposed to sunlight are greyed-orange, nearest to in between 166A and 166B.

*Color of bark on main stems.*—Greyed-brown, nearest to RHS 199A.

Foliage:

*Arrangement.*—Opposite.

*Division.*—Simple.

*Quantity.*—Average of 10 leaves per lateral branch.

*Lamina.*—Dimensions — 6.2 cm long and 4.6 cm wide, on average. Shape — Broad obovate to broad elliptic. Aspect — Flat to very slightly carinate. Apex — Short apiculate to abruptly acute. Base — Rounded to truncate. Margin — Entire; not undulated. Pubescence, texture and luster of adaxial surface — Glabrous, smooth, and moderately glossy. Pubescence, texture and luster of abaxial surface — Glabrous, smooth, and slightly glossy. Color — Juvenile foliage, adaxial surface — Yellow-green, nearest to RHS 146A yet slightly darker. Juvenile foliage, abaxial surface — Yellow-green, nearest to RHS 146A. Mature foliage, adaxial surface — Nearest to in between yellow-green and greyed-green; RHS 147A and N189A yet darker. Mature foliage, abaxial surface — Yellow-green, nearest to in between RHS 146B and 147B. Venation — Pattern — Pinnate. Venation color, adaxial surface — Green, nearest to RHS 143B. Venation color, abaxial surface — Yellow-green, nearest to RHS 145B.

*Petiole.*—Length — 1.5 cm. Width — 0.15 cm. Texture — Smooth and glabrous. Luster — Slightly glossy. Strength — Somewhat strong. Color, adaxial surface — Yellow-green, nearest to RHS 148A. Color, abaxial surface — Yellow-green, nearest to RHS 144C.

Inflorescence:

*Inflorescence Arrangement.*—Axillary raceme bearing 4 to 8 flowers.

*Natural flowering season.*—Long flowering period; spring through autumn in USDA Hardiness Zones 10 through 12.

*Time to flower.*—Repeating approximately every 10 weeks.

*Dimensions.*—13.8 cm high and 10.3 cm in diameter.

*Quantity of flowers per inflorescence.*—3 on average; varying from 2 to 5.

*Quantity of flower buds per plant.*—65.

*Quantity of flowers and flower buds per plant.*—120, including senesced flowers.

*Peduncle.*—Dimensions — 9.3 cm long and 0.2 cm in diameter. Aspect — Upward and outward; at approximately 35 degrees to the lateral branch axis. Strength — Moderately strong. Texture and luster — Glabrous and glossy. Color — Yellow-green, nearest to in between RHS 144A and 146B.

Bud:

*Shape.*—Narrow oblanceolate.

*Dimensions.*—5.5 cm long and 1.0 cm in diameter.

*Pubescence, texture and luster.*—Glabrous, smooth and very slightly glossy.

*Color.*—The distal one-quarter portion of the bud is red, nearest to RHS 50C; the middle portion is yellow-green, nearest to RHS 145C; and, the proximal one-third portion of the bud is yellow-green, nearest to RHS 145A.

Flower:

*Flowering habit.*—Moderately free flowering.

*Shape.*—Funnelform.

*Flower vertical height.*—8.4 cm.

*Flower width.*—8.4 cm.

*Flower length.*—6.7 cm.

*Diameter of floral throat.*—1.7 cm, at its widest point.

*Floral throat texture.*—Glabrous; smooth.

*Diameter of floral tube.*—1.8 cm at the distal end; at approximately one-third of the distance from the base, where tube begins to widen, the diameter is 0.35 cm.

*Length of floral tube.*—5.0 cm.

*Floral tube texture.*—Glabrous; smooth.

*Attitude.*—Flowers are outward facing.

*Fragrance.*—A faint pleasant fragrance; acidic-sweet.

*Lastingness.*—Approximately 10 days.

*Persistent.*—Self-cleaning.

*Pedicels.*—Dimensions — 0.8 cm long and 0.25 cm in diameter. Aspect — Upward and outward; approximately 30 degrees to the peduncle axis. Strength — Moderately strong. Texture and luster — Glabrous, smooth, and moderately glossy. Color — Yellow-green, nearest to RHS 152B.

*Petals.*—Quantity of Petals — 5. Arrangement — Single whorl; petals imbricate and fused into an elongated tube at the base; lower 60 percent of the petals are fused. Attitude — Petals are outstretched at nearly 90 degrees to the floral tube. Shape of petal lobes — Spatulate. Dimensions, free portion of petals — 8.9 cm long and 4.5 cm wide. Apex — Unequal short apiculate. Base — Truncate; fused at the base. Margin — Entire; moderately to highly undulated. Aspect — Moderately reflexed. Pubescence, texture and luster of upper surface — Glabrous, velvety and slightly glossy. Pubescence, texture and luster of lower surface — Glabrous, moderately velvety and slightly glossy. Petal lobe color when opening, upper surface — Red-purple, nearest to RHS 62C, and lightly suffused with a lighter shade of red-purple, nearest to RHS 69C. Petal lobe color when opening, lower surface — Red-purple, nearest to RHS 65B; central longitudinal band and base of the petals near the floral throat are red-purple, RHS 62C. Petal lobe color when fully opened, upper surface — Red-purple, nearest to RHS 62C, and lightly suffused with a lighter shade of red-purple, nearest to RHS 69C. No visible venation. Color do not fade with age. Petal lobe color when fully opened, lower surface — Red-purple, nearest to RHS 65B; central longitudinal band and base of the petals near the floral throat are red-purple, RHS 62C. No visible venation. Colors do not fade with age. Floral throat color — Red-purple, nearest to a mixture of RHS 62B and 62C, and suffused with a darker shade of red-purple, nearest to RHS 61D. Floral throat venation color — Red-purple, nearest to RHS 61D. Inner corolla tube color, when fully opened — Red, nearest to RHS 52C, and fading to orange-red, distally, nearest to RHS 34B; distal-most portion of the tube at the floral throat is yellow-green, nearest to a mixture of RHS 151C and 151D. Fading to white towards the throat, nearest to RHS NN155A. Veined yellow-orange, nearest to a mixture of RHS 22A and 22B. Outer corolla tube color, when fully opened — Red-purple, nearest to RHS 65D; distal portion of the tube is yellow-green, nearest to RHS 145A, and heavily suffused with a darker shade of yellow-green, nearest to RHS 152B. No visible venation.

*Calyx.*—Shape — Rotate; single whorl of sepals. Dimensions — 0.8 cm in diameter and 0.5 cm tall. Sepals — Arrangement — Sepals are free, rotate. Quantity — 5. Shape — Narrow triangular to lanceolate. Apex — Narrow acuminate. Base — Cuneate. Margin — Entire; not undulated. Pubescence, texture and luster, upper surface — Smooth; glabrous; slightly glossy. Pubescence, texture and luster, lower surface — Smooth; glabrous; very slightly glossy. Color when opening, upper surface — Yellow-green, nearest to RHS 145C; apex is greyed-red, nearest to RHS 179C. Color when opening, lower surface — Yellow-green, nearest to RHS 146D; apex is greyed-red, nearest to RHS 179C. Color when fully opened, upper surface — Yellow-green, nearest to RHS 145C; apex is greyed-red, nearest to RHS 179C. Color when fully opened, lower surface — Yellow-green, nearest to RHS 145C; apex is greyed-red, nearest to RHS 179C.

Reproductive organs:

*Androecium.*—Stamen quantity — 5. Attachment — Adnate. Filament length — 0.2 cm. Filament color — Yellow-green, nearest to RHS 154B. Inner side of the filament is densely pubescent with short white hairs, approximately 0.8 mm long, colored nearest to RHS NN155D. Anther attachment — Basifixed. Anther shape — Narrow sagitate. Anther length — 1.0 cm. Anther width — 0.15 cm. Anther color — Greyed-yellow, nearest to RHS 162B. Anther aspect — The five anthers are touching at their apices, thus forming a cone of anthers. Pollen, presence — Scarce. Pollen color — White, RHS 155A.

*Gynoecium.*—Pistil quantity — One. Pistil length — 2.5 cm. Style length — 2.3 cm. Style color — Yellow-green, nearest to RHS 145D. Stigma shape — Club-shaped. Stigma length — 0.2 cm. Stigma diameter — 0.2 cm. Stigma color — Yellow-green, nearest to a mixture of RHS 145A and 145B. Ovary color — Yellow-green, nearest to RHS 144C.

Seed and fruit: None observed.

Comparisons with the parent plant: Plants of the new cultivar 'PATMANROS2' differ from the unnamed *Mandevilla sanderi* (not patented) parent by the characteristics described in Table 1.

TABLE 1

| Characteristic | 'PATMANROS2' | Unnamed parent |
|---|---|---|
| Growth habit. | More densely foliaged than the parent. | Less densely foliaged than 'PATMANROS2'. |
| Floral aspect at anthesis. | More open than the parent. | Less open than 'PATMANROS2'. |

Comparison with the most similar *Mandevilla* cultivar known to the inventor: Plants of the new cultivar 'PATMANROS2' differ from the commercial variety, *Mandevilla* 'PATMANCR' (U.S. Pat. No. 29,797), in the following characteristics described in Table 2 below.

TABLE 2

| Characteristic | 'PATMANROS2' | 'PATMANCR' |
|---|---|---|
| Growth habit. | More basal and lateral branching than 'PATMANCR'. | Less basal and lateral branching than 'PATMANROS2'. |
| Abundance of foliage. | More abundant than 'PATMANCR'. | Less abundant than 'PATMANROS2'. |
| Foliage shape. | Broader than 'PATMANCR'. | Narrower than 'PATMANROS2'. |

TABLE 2-continued

| Characteristic | 'PATMANROS2' | 'PATMANCR' |
|---|---|---|
| Quantity of floral buds and flowers. | More abundant than 'PATMANCR'. | Less abundant than 'PATMANROS2'. |
| General coloration of the flower. | Lighter shade of red-purple. | Darker shade of red-purple. |
| Floral aspect at anthesis. | More open than 'PATMANCR'. | Less open than 'PATMANROS2'. |

That which is claimed is:

1. A new and distinct *Mandevilla* plant named 'PATMANROS2', substantially as described and illustrated herein.

* * * * *